United States Patent
Caserta et al.

(10) Patent No.: US 7,243,859 B2
(45) Date of Patent: Jul. 17, 2007

(54) ADJUSTABLE NON-ELECTRIC LIQUID AIR FRESHENER DEVICE

(75) Inventors: Andrea Caserta, Barcelona (ES); Ruben Garcia Fabrega, Barcelona (ES); David Moreno Perez, Barcelona (ES)

(73) Assignee: Zobele Españ a, S.A., Barcelona (ES)

( * ) Notice: Subject to any disclaimer, the term of this patent is extended or adjusted under 35 U.S.C. 154(b) by 325 days.

(21) Appl. No.: 10/527,988

(22) PCT Filed: Jun. 12, 2003

(86) PCT No.: PCT/ES03/00291

§ 371 (c)(1),
(2), (4) Date: Mar. 21, 2005

(87) PCT Pub. No.: WO2004/110559

PCT Pub. Date: Dec. 23, 2004

(65) Prior Publication Data

US 2006/0016904 A1    Jan. 26, 2006

(51) Int. Cl.
*A24F 25/00* (2006.01)
*A61L 9/04* (2006.01)

(52) U.S. Cl. .............. 239/34; 239/44; 239/47; 239/49; 239/50; 239/51.5; 239/55; 239/57

(58) Field of Classification Search .......... 239/34, 239/44, 47, 49, 50, 51.5, 55, 57
See application file for complete search history.

(56) References Cited

U.S. PATENT DOCUMENTS

| 4,621,768 A | 11/1986 | Lhoste et al. |
| 4,732,321 A * | 3/1988 | Dolan ................ 239/45 |
| 4,739,928 A | 4/1988 | O'Neil |
| 4,742,960 A * | 5/1988 | Bustillo et al. ........ 239/47 |
| 4,928,881 A | 5/1990 | Barlies et al. |
| 5,121,881 A * | 6/1992 | Lembeck .............. 239/44 |
| 5,725,152 A | 3/1998 | Akyu |

OTHER PUBLICATIONS

International Search Report dated Nov. 19, 2003, in PCT/ES2003/00291.

* cited by examiner

*Primary Examiner*—Davis Hwu
(74) *Attorney, Agent, or Firm*—McDermott Will & Emery LLP

(57) ABSTRACT

Comprises a vessel (1) containing scented liquid, a wick (2) partially submerged in the liquid, a stopper (3) coupled on the mouth (7) of the vessel (1) and a cap (5) that covers the stopper (3) and has a lower tubular portion (11) provided with two windows (15) and an inner threaded segment that unscrews from a central threaded tubular portion (13) of the stopper (3) as the cap (5) is turned, raising it and gradually revealing the windows (15) so that the wick (2) is exposed to the exterior, facilitating the adjustable evaporation of the scented liquid, the cap (5) being provided with flexible stops (16) that are prolonged externally from the base of its lower tubular portion (11) and as they rise meet a trapezoidal inner peripheral flange (17) defined in a cylindrical body (14) of the stopper (3) to prevent the exit of the cap (5).

4 Claims, 6 Drawing Sheets

ADJUSTABLE NON-ELECTRIC LIQUID AIR FRESHENER DEVICE

OBJECT OF THE INVENTION

This invention relates to a non-electric liquid air freshener with a wick that allows an adjustable evaporation of the scented liquid by a wick having a segment submerged in the scented liquid contained in a vessel and another segment exposed to the air to facilitate the evaporation of the liquid in the vessel.

The object of the invention is for the air freshener to incorporate a cap with windows that expose the wick to the air as these windows are opened when the cap is unscrewed from a stopper of the vessel.

Also the object of the invention is that the cap incorporates means to prevent the separation of the cap from the stopper in its position of maximum aperture, as well as providing the stopper with means to prevent its rotation and extraction from the vessel.

BACKGROUND OF THE INVENTION

Air fresheners of several types are known in the market. Worth mention are those that do not require the use of electricity and consist of a vessel containing the scented liquid or perfume and allow the exit of a wick that is partially in contact with the scented liquid, from where the scent is diffused outwards, and other air fresheners that require electricity to drive an inner fan that helps distribute the scent of the scented liquid in the premises in which it is located.

The invention disclosed herein belongs to the group of non-electrical air fresheners.

Worth mention within the field including this type of air fresheners is the invention patent ES1 051 172, which relates to an air freshener device consisting of a perfume-containing vessel that in position of non-use closes its mouth with a cap that is completed with other means to transfer the perfume in the vessel to the surroundings.

More specifically, the air freshener device incorporates associated to its threaded cap a wick support that hangs internally in the vessel and in its vertical displacement rubs against a guide stopper inserted internally in the mouth of the vessel. The amount of perfume diffused is regulated by changing the portion of the wick that projects above the vessel by pulling the cap manually upwards, stabilising the various possible positions of the wick by its rubbing with the guide stopper. This system for adjusting and stabilising the position of the wick based on mutual continuous friction leads to an early wear of these surfaces that makes the air freshener useless after a short time.

On the other hand, this patent considers the incorporation of hooks on the back end of the wick support, so that when the wick support reaches its position of maximum extraction these act as stops in the rear edge of the stopper to prevent its exit. The repeated contact of the hooks and the stopper causes a deformation of the wick support that results in a reduced positional stability of the wick.

Invention patent ES 2 160 033 belonging to the applicant of the present invention discloses a stopper for vessels containing evaporable liquids having an annular body with a neck for coupling and retention on the opening of a vessel provided with an axial passage for positioning the wick that incorporates means for retaining and immobilising the wick that together prevent the vessel from being refilled.

In the latter invention patent, as well as in the one cited before, the possibility is not considered of a stable system that allows changing the exposed surface of the wick and thus regulating the evaporation, which is the object of the invention described hereunder.

DESCRIPTION OF THE INVENTION

The air freshener disclosed in this invention is of the liquid non-electrical type, and mainly stands out in that it facilitates an adjustable evaporation by opening windows made in a cap that gradually expose a wick that is partially submerged in a vessel with scented liquid when unscrewed vertically from a stopper coupled to the vessel containing the scented liquid.

The air freshener also stands out for incorporating a system for locking the position of maximum aperture, which prevents the cap from being removed from the stopper, as well as incorporating a system to prevent the extraction of the stopper from the vessel and an anti-rotation system that prevents the stopper from turning about the neck of the vessel when the cap turns.

The cap basically comprises an upper cylindrical body, an intermediate crown with a flat base in which are defined to large openings from which extend downwards corresponding windows made in a lower tubular segment that is in turn provided with an inner threaded segment meant to be coupled in the outer threaded segment defined in a central tubular portion of the stopper.

The stopper has an upper annular body with a conical surface for coupling and retention on the vessel neck or opening, and is inferiorly prolonged as a cylindrical body that after two elbows is extended as the aforementioned central tubular portion of the stopper, from which in turn arises a neck between the inner walls of which the wick is fitted in a vertical position.

Thus, starting from the closed position between the cap and stopper, when the cylindrical body of the cap is turned its lower tubular portion is unscrewed from the central tubular portion of the stopper, the cap rising and gradually opening its windows, exposing the wick to the air to allow the perfume to evaporate. As the cap rises a greater length of the wick is exposed and the perfume evaporates more, thereby regulating the amount of perfume diffused.

To prevent the total extraction of the cap from the stopper the cap is provided with flexible stops that run externally from the base of its lower tubular portion and slide over the inner walls of the cylindrical body of the stopper as the cap is displaced, until they meet a trapezoidal inner peripheral flange made in said body that prevents the exit of the cap.

The initial assembly of the cap on the stopper is facilitated by the flexibility of the stops and the slight inclination of the peripheral flange on-its upper face, so that the flexible stop must overcome the flange until it is under it, after which it cannot be removed. TO this end, the peripheral flange has a nearly horizontal inclination on its bottom face that prevents the exit of the flexible stop and can even be deformed without allowing the extraction of the cap.

In addition, the annular stopper body has inner elbows that clip onto the flange of the vessel mouth to prevent its extraction.

Similarly, the outer wall of the mouth is provided with a series of thickened areas that constitute stops for the aforementioned elbows of the annular stopper body, preventing it from turning about the vessel.

As regards the union between the cap and the stopper, the neck of the stopper is provided with a conical recess with an inclination equal to the inclination of a lower extension of the cap handle that passes under the flat base of the intermediate crown, so that in the closed position with the cap screwed on the stopper, the recess of the lower extension of the cap handle will be coupled in contact with the recess of the stopper neck.

DESCRIPTION OF THE DRAWINGS

To complete the description being made an in order to aid a better understanding of the characteristics of the invention, according to an example of a preferred embodiment, the description is accompanied by a set of drawings that form an integral part of the description and where, for purposes of illustration and in a non-limiting sense, the following is shown.

PREFERRED EMBODIMENT OF THE INVENTION

Figure 1:
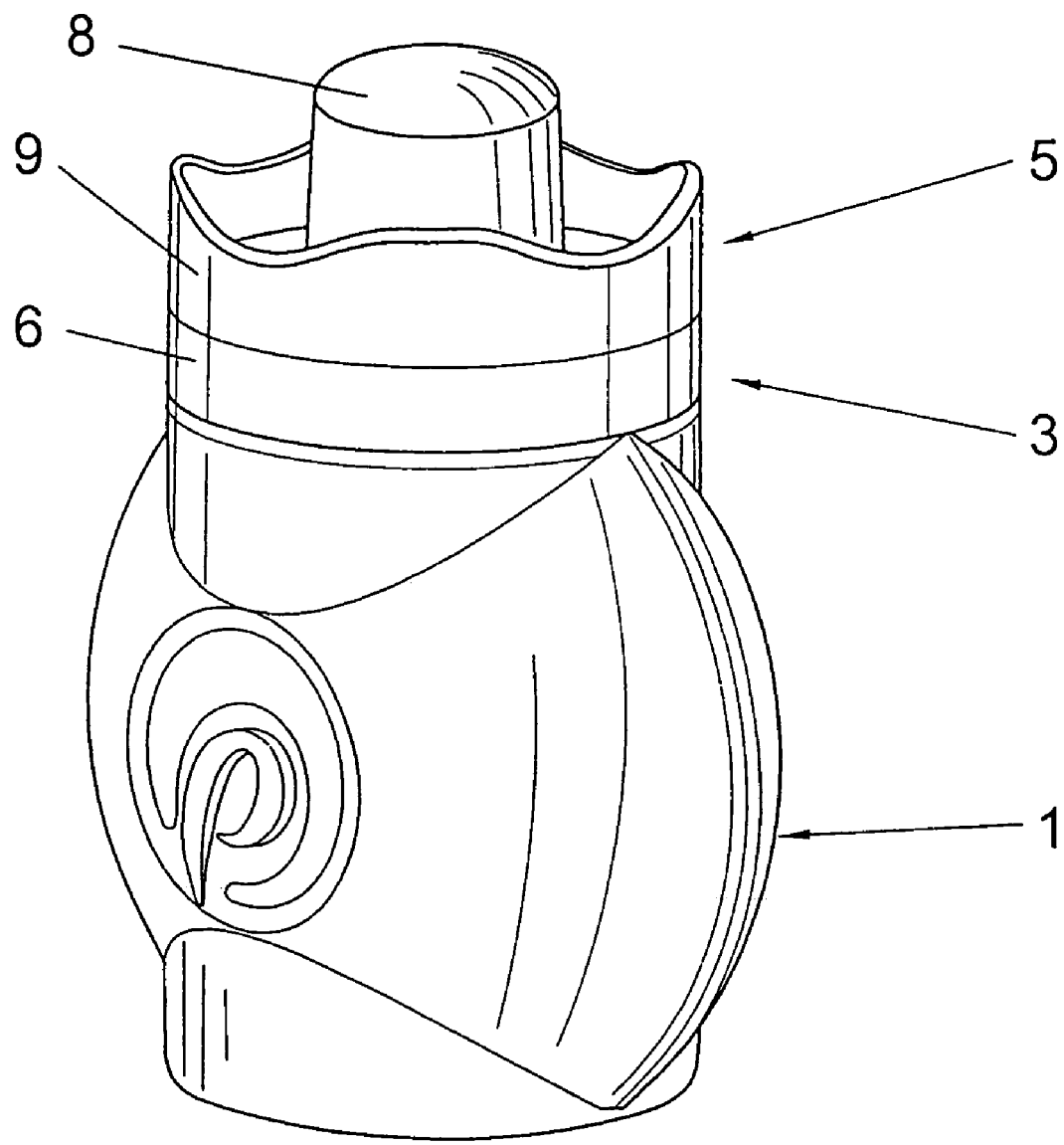
FIG. 1. Shows a perspective view of the air freshener in its closed position.
Figure 2:
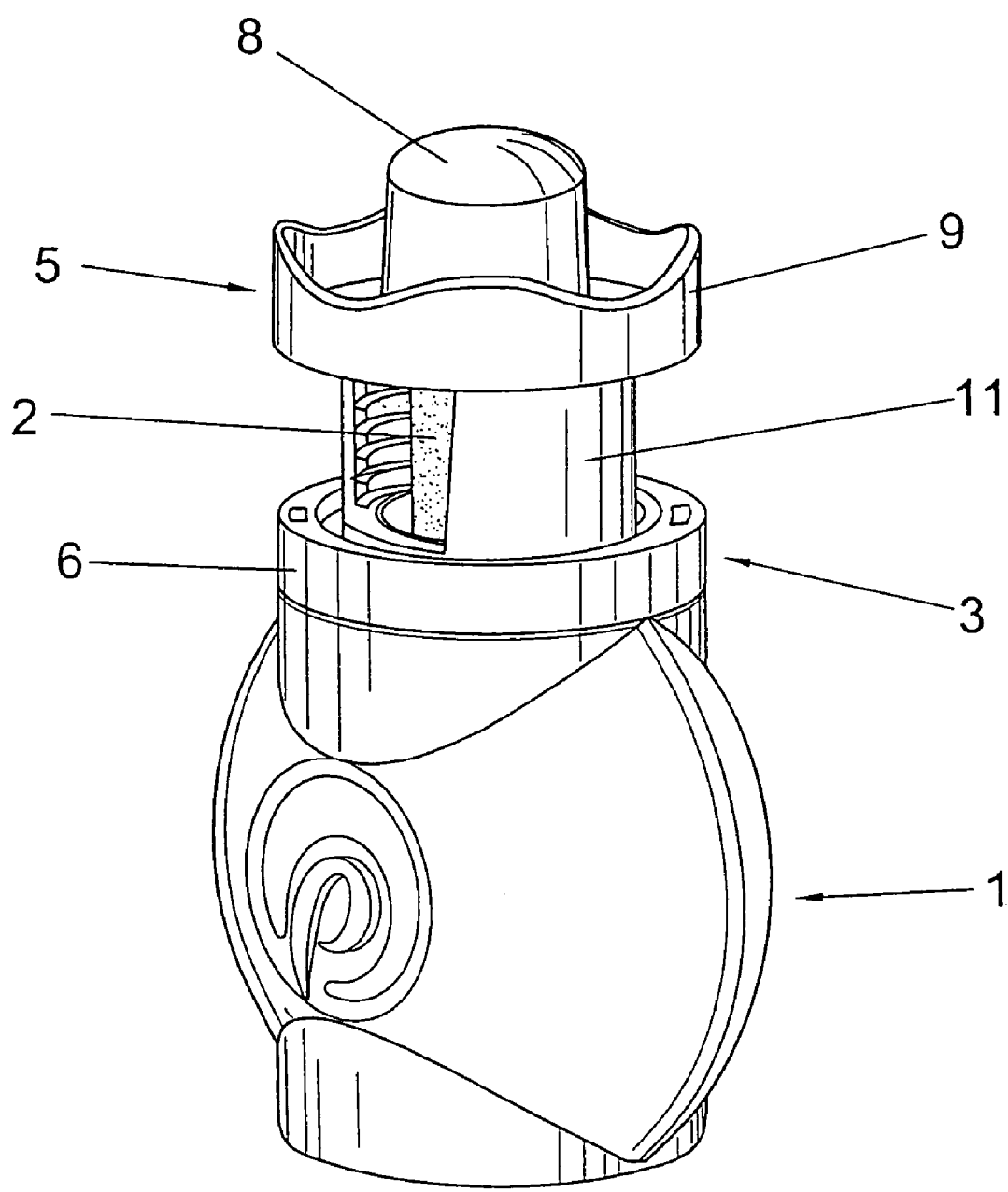
FIG. 2. Shows a perspective view of the air freshener in its open position in the situation in which the cap windows are uncovered, exposing the wick to the air.
Figure 3:
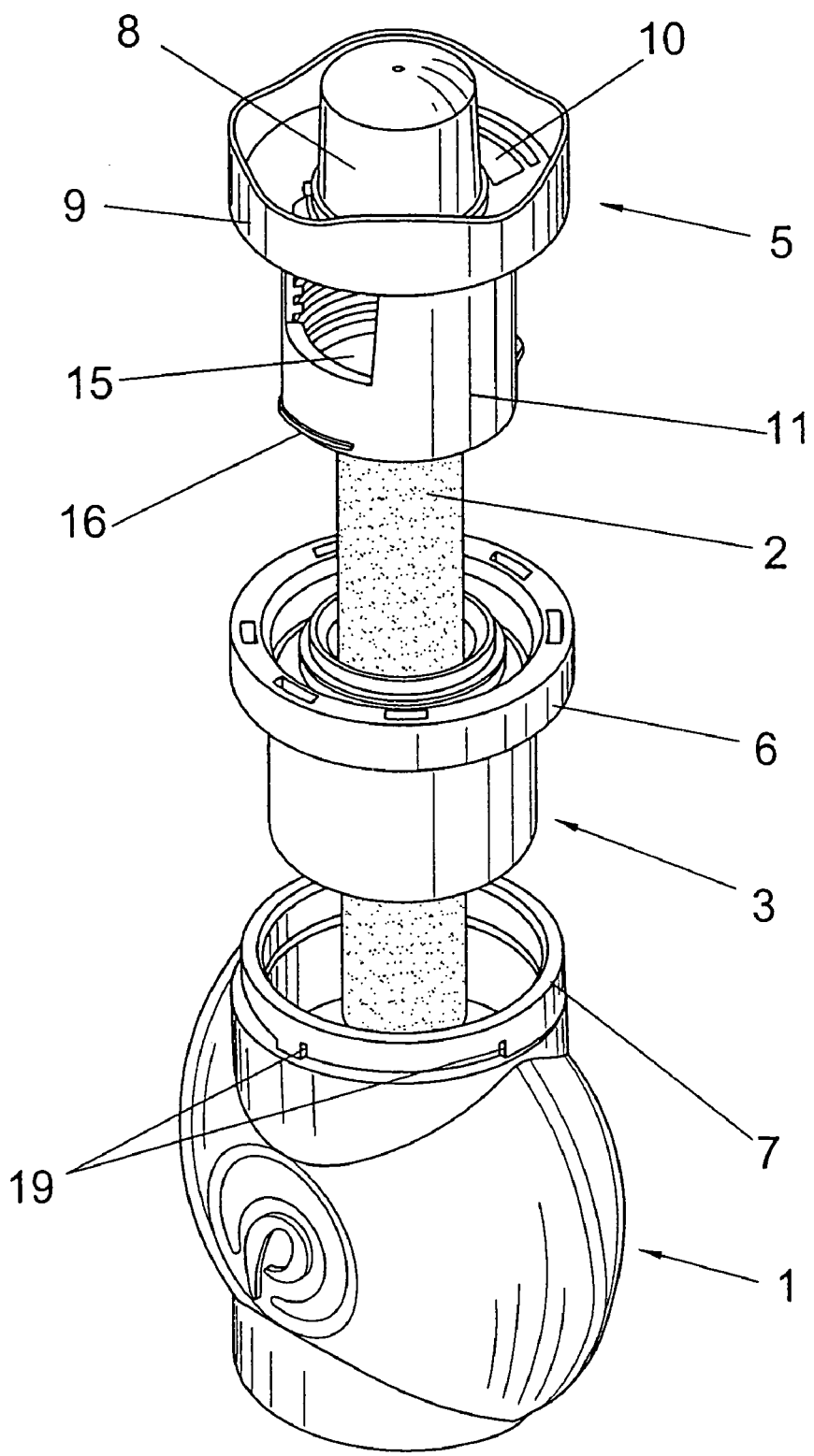
FIG. 3. Shows an exploded view of the air freshener in which its component elements can be seen.
Figure 4:
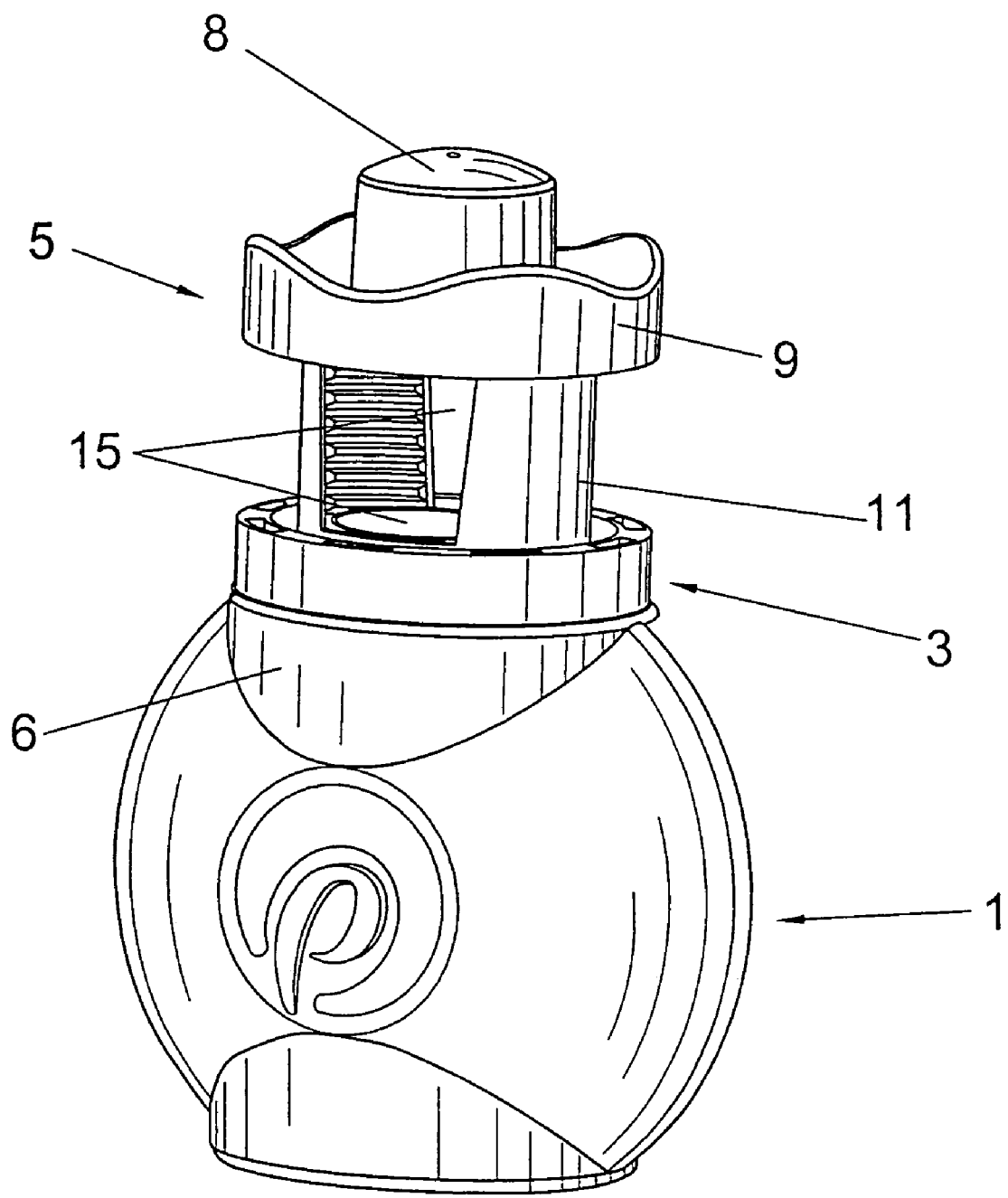
FIG. 4. Shows a perspective view of the air freshener in its open position where the wick has not been depicted in order to facilitate the view of the two windows and the inner thread of the lower tubular portion of the cap.
Figure 5:
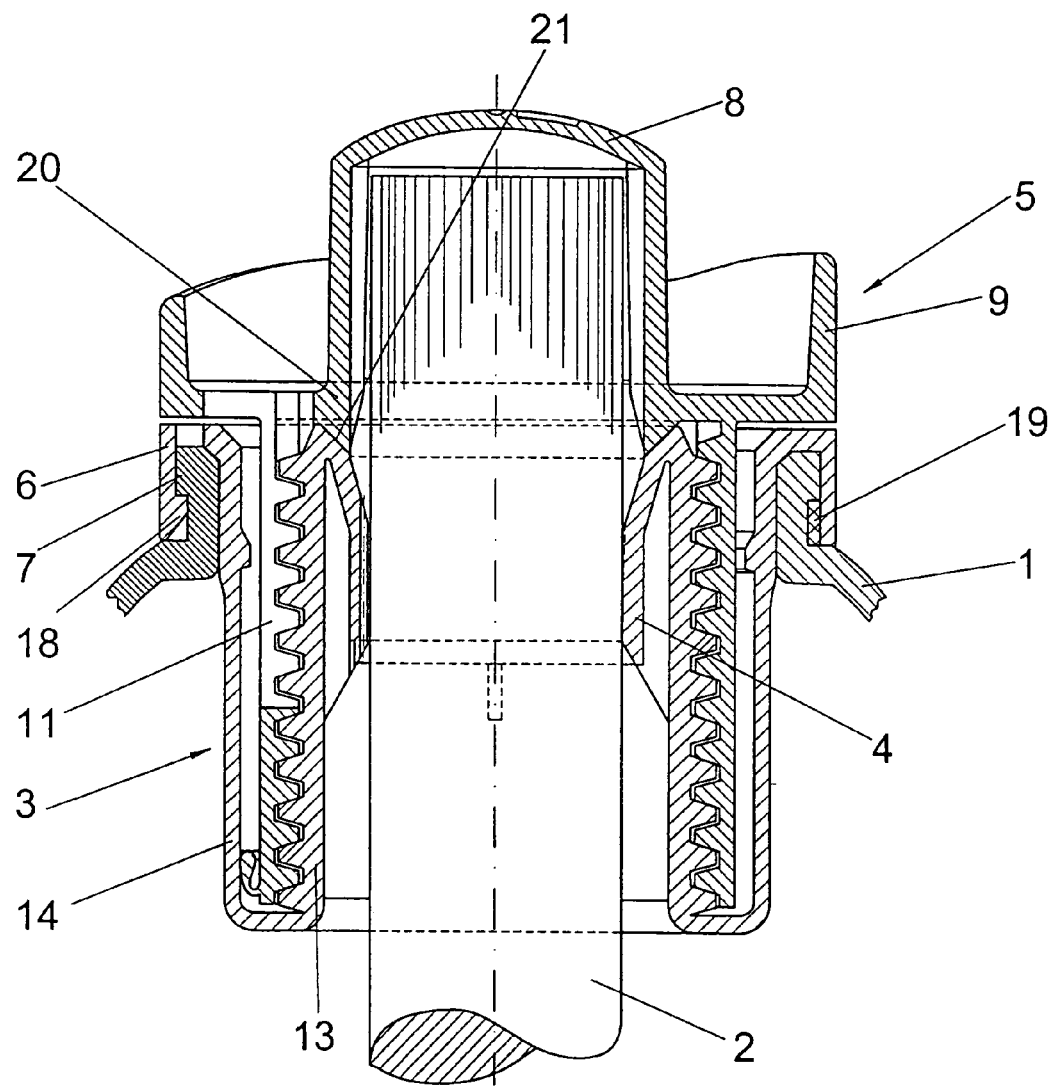
FIG. 5. Shows a sectional elevation view of the air freshener in its closed position.
Figure 6:
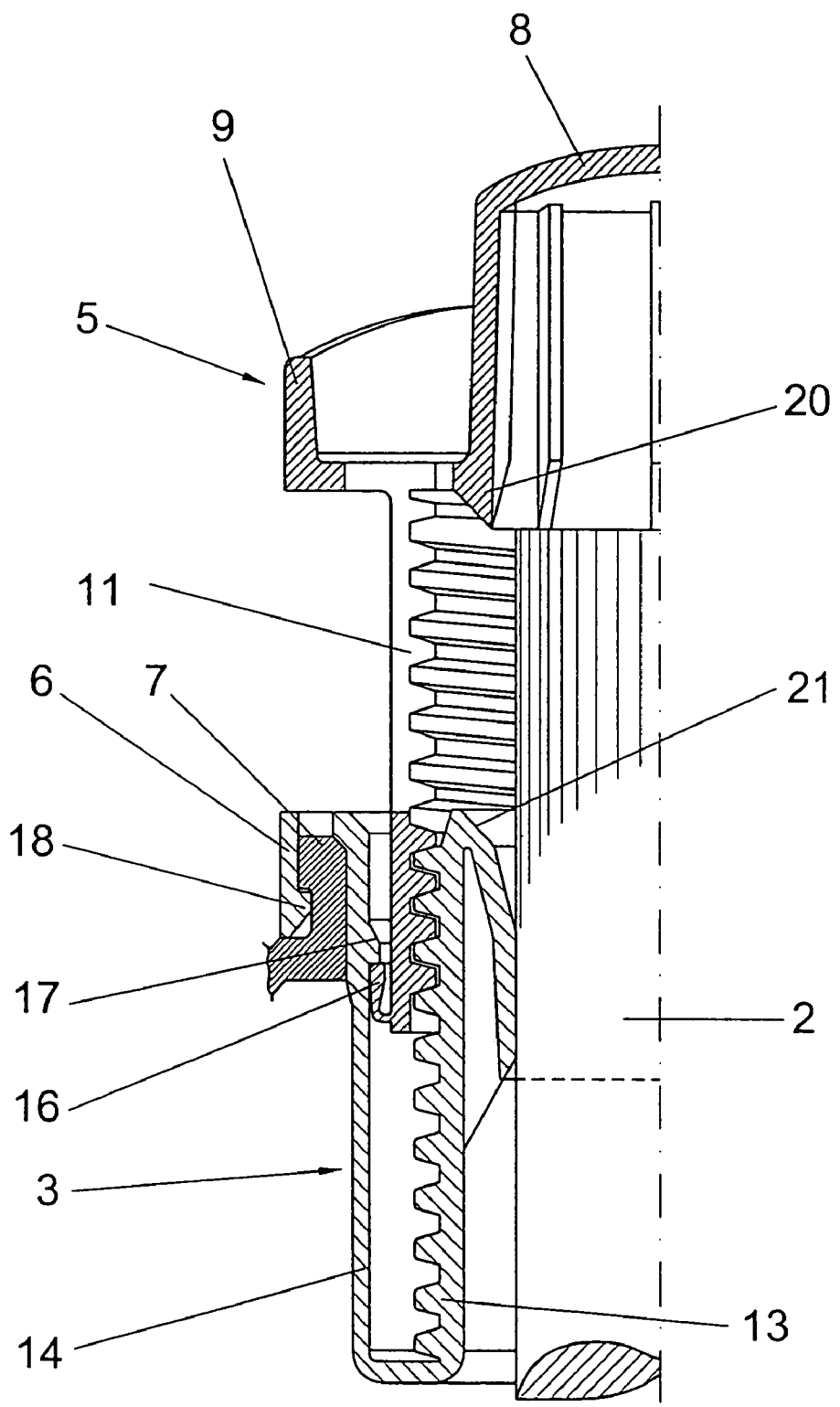
FIG. 6. Shows a sectional elevation view of half of the air freshener in its open position with an enlarged view of the flexible stop.

The air freshener object of this invention is of the liquid non-electrical type comprising a vessel (1) that contains a scented liquid, a wick (2) partially submerged in the scented liquid that is fitted vertically in the neck (4) of a stopper (3) provided with an upper annular body (6) with lower internal elbows (18) for coupling and retention on the mouth (7) of the vessel (1), and a cap (5) that covers the stopper (3).

From this basic configuration, the air freshener mainly stands out in that the cap (5) comprises an upper cylindrical body (8), an intermediate crown (9) with a flat base in which two large openings (10) are defined and a lower tubular portion (11) with two windows (15) that extend below the openings (10), which shows an inner threaded segment that unscrews from a central threaded tubular segment (13) of the stopper (3) as the cap (5) is turned, raising it and gradually revealing the windows (15) so that the wick (2) is exposed to the exterior, facilitating the adjustable evaporation of the scented liquid, said central threaded tubular segment (13) being located between the neck (4) and a cylindrical body (14) that prolongs downward from the upper annular body (6) of the stopper (3).

In addition, the cap (5) is provided with flexible stops (16) that prolong externally from the base of its lower tubular portion (11) and slide on the inner walls of the cylindrical body (14) of the stopper (3) as the cap (5) moves until they meet a trapezoidal inner peripheral flange (17) defined in said cylindrical body (14) that prevents the exit of the cap (5).

The trapezoidal flanges (17) have a slight inclination in the upper face to allow the flexible stop (16) to overcome them in its initial assembly, and have a nearly horizontal inclination on their lower face that prevents the exit of the flexible stop (16) and thus the extraction of the cap (5).

It is foreseen that the outer wall of the mouth (7) of the vessel (1) has a number of thickened areas (19) that constitute stops for the inner elbows (18) of the annular body (6) of the stopper (5), preventing the latter from turning about the vessel (1).

In addition, the cylindrical body (8) of the cap (5) incorporates a lower extension (20) that passes below the base of the crown (9) and is provided with a recess with an inclination equal to that of a recess (21) made in the upper segment of the neck (4) of the stopper (3) to establish a contact between the two surfaces in the closed position, ensuring the seal.

The invention claimed is:

1. Adjustable non-electrical liquid air freshener comprising a vessel (1) containing scented liquid, a wick (2) partially submerged in the scented liquid that is fitted vertically in the neck (4) of a stopper (3) provided with an upper annular body (6) with lower internal elbows (18) for coupling and retention on the mouth (7) of the vessel (1), and a cap (5) that covers the stopper (3), essentially characterised in that the cap (5) comprises an upper cylindrical body (8), an intermediate crown (9) with a flat base in which two large openings (10) are defined and a lower tubular portion (11) with two windows (15) that extend below the openings (10) and an inner threaded segment that unscrews from a central threaded tubular segment (13) of the stopper (3) as the cap (5) is turned, raising it and gradually revealing the windows (15) so that the wick (2) is exposed to the exterior, facilitating the adjustable evaporation of the scented liquid, said central threaded tubular segment (13) being located between the neck (4) and a cylindrical body (14) that prolongs downward from the upper annular body (6) of the stopper (3), the cap (5) being provided with flexible stops (16) that are prolonged externally from the base of its lower tubular portion (11) and slide on the inner walls of the cylindrical body (14) of the stopper (3) as the cap (5) moves until they meet a trapezoidal inner peripheral flange (17) defined in said cylindrical body (14) that prevents the exit of the cap (5).

2. Adjustable non-electrical liquid air freshener according to claim 1, characterised in that the trapezoidal flanges (17) have a slight inclination in their upper face to allow the flexible stop (16) to overcome them in its initial assembly, and have a nearly horizontal inclination on their lower face that prevents the exit of the flexible stop (16) and thus the extraction of the cap (5).

3. Adjustable non-electrical liquid air freshener according to claim 1, characterised in that it has a number of thickened areas (19) on the outer wall of the mouth (7) of the vessel (1) that constitute stops for the inner elbows (18) of the annular body (6) of the stopper (5), preventing the latter from turning about the vessel (1).

4. Adjustable non-electrical liquid air freshener according to claim 1, characterised in that the handle (8) of the cap (5) incorporates a lower extension (20) that passes below the base of the crown (9) and is provided with a recess with an inclination equal to that of a recess (21) made in the upper segment of the neck (4) of the stopper (3) to establish a contact between the two surfaces in the closed position, ensuring the seal.

* * * * *